(12) United States Patent
Artsyukhovich et al.

(10) Patent No.: US 8,573,801 B2
(45) Date of Patent: Nov. 5, 2013

(54) LED ILLUMINATOR

(75) Inventors: Alexander N. Artsyukhovich, San Juan Capistrano, CA (US); Michael J. Papac, Tustin, CA (US); Ronald T. Smith, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 286 days.

(21) Appl. No.: 13/234,259

(22) Filed: Sep. 16, 2011

(65) Prior Publication Data
US 2012/0051042 A1 Mar. 1, 2012

Related U.S. Application Data

(63) Continuation-in-part of application No. 13/208,974, filed on Aug. 12, 2011, now abandoned.

(60) Provisional application No. 61/378,206, filed on Aug. 30, 2010.

(51) Int. Cl.
F21V 33/00 (2006.01)

(52) U.S. Cl.
USPC .......................................... 362/234; 362/231

(58) Field of Classification Search
USPC ........... 362/221, 243, 234, 231; 351/221, 243
See application file for complete search history.

(56) References Cited

U.S. PATENT DOCUMENTS

| | | |
|---|---|---|
| 3,026,559 A | 3/1962 | Rappaport |
| 4,222,375 A | 9/1980 | Martinez |
| 4,656,508 A | 4/1987 | Yokota |
| 4,870,952 A | 10/1989 | Martinez |
| 4,883,333 A | 11/1989 | Yanez |
| 4,884,133 A | 11/1989 | Kanno et al. |
| 5,086,378 A | 2/1992 | Prince |
| 5,301,090 A | 4/1994 | Hed |
| 5,420,768 A | 5/1995 | Kennedy |
| 5,465,170 A | 11/1995 | Arimoto |
| 5,526,190 A | 6/1996 | Hubble, III et al. |
| 5,591,160 A | 1/1997 | Reynard |
| 5,598,042 A | 1/1997 | Mix et al. |

(Continued)

FOREIGN PATENT DOCUMENTS

| | | |
|---|---|---|
| EP | 1114608 B1 | 3/2003 |
| JP | 2006087764 A | 4/2006 |
| WO | 00/54655 A1 | 9/2000 |
| WO | 2008/133736 A2 | 11/2008 |

OTHER PUBLICATIONS

Yasujima, H., et al; JP2006087764A, Publication Date Apr. 6, 2006; Abstract only—machine translation; espacenet.com.

(Continued)

*Primary Examiner* — Julie Shallenberger
(74) *Attorney, Agent, or Firm* — Keiko Ichiye

(57) ABSTRACT

Disclosed is an exemplary illumination device for enhancing the brightness and chromaticity of an illuminator employing light emitting diodes (LED). The illumination device may include a first light source configured to emit light at a first wavelength range. A first dichroic optical element associated with the first light source may be configured to optically block less than the entire wavelength range of the light emitted from the first light source. The illumination device may also include a second light source configured to emit light at second wavelength range substantially corresponding to the wavelength range optically blocked by the first dichroic optical element.

13 Claims, 8 Drawing Sheets

(56) References Cited

U.S. PATENT DOCUMENTS

| | | | |
|---|---|---|---|
| 5,634,711 A | 6/1997 | Kennedy et al. | |
| 5,657,116 A | 8/1997 | Kohayakawa | |
| 5,736,410 A | 4/1998 | Zarling et al. | |
| 5,830,139 A | 11/1998 | Abreu | |
| 5,859,693 A | 1/1999 | Dunne et al. | |
| 5,997,163 A | 12/1999 | Brown | |
| 6,000,813 A | 12/1999 | Krietzman | |
| 6,015,403 A | 1/2000 | Jones | |
| 6,036,683 A | 3/2000 | Jean et al. | |
| 6,102,696 A | 8/2000 | Osterwalder et al. | |
| 6,120,460 A | 9/2000 | Abreu | |
| 6,123,668 A | 9/2000 | Abreu | |
| D434,753 S | 12/2000 | Druckenmiller et al. | |
| 6,183,086 B1 | 2/2001 | Neubert | |
| 6,190,022 B1 | 2/2001 | Tocci et al. | |
| 6,211,626 B1 | 4/2001 | Lys et al. | |
| 6,213,943 B1 | 4/2001 | Abreu | |
| 6,217,188 B1 | 4/2001 | Wainwright et al. | |
| 6,226,126 B1 | 5/2001 | Conemac | |
| 6,268,613 B1 | 7/2001 | Cantu et al. | |
| 6,270,244 B1 | 8/2001 | Naum | |
| 6,272,269 B1 | 8/2001 | Naum | |
| 6,336,904 B1 | 1/2002 | Nikolchev | |
| 6,431,731 B1 | 8/2002 | Krietzman | |
| 6,436,035 B1 | 8/2002 | Toth et al. | |
| 6,459,844 B1 | 10/2002 | Pan | |
| 6,730,940 B1 | 5/2004 | Steranka et al. | |
| 6,786,628 B2 | 9/2004 | Steen et al. | |
| 6,893,258 B1 | 5/2005 | Kert | |
| 6,917,057 B2 | 7/2005 | Stokes et al. | |
| 6,960,872 B2 | 11/2005 | Beeson et al. | |
| 7,025,464 B2 | 4/2006 | Beeson et al. | |
| 7,063,436 B2 | 6/2006 | Steen et al. | |
| 7,229,202 B2 | 6/2007 | Sander | |
| 7,234,820 B2 * | 6/2007 | Harbers et al. | 353/94 |
| 7,276,737 B2 | 10/2007 | Camras et al. | |
| 7,301,271 B2 | 11/2007 | Erchak et al. | |
| 7,325,957 B2 | 2/2008 | Morejon et al. | |
| 7,344,279 B2 | 3/2008 | Mueller et al. | |
| 7,349,163 B2 | 3/2008 | Angelini et al. | |
| 7,403,680 B2 | 7/2008 | Simbal | |
| 7,482,636 B2 | 1/2009 | Murayama et al. | |
| 7,494,228 B2 | 2/2009 | Harbers et al. | |
| 7,556,412 B2 | 7/2009 | Guillermo | |
| 7,561,329 B2 | 7/2009 | Zahniser et al. | |
| 7,682,027 B2 | 3/2010 | Buczek et al. | |
| 7,918,583 B2 | 4/2011 | Chakmakjian et al. | |
| 7,990,587 B2 | 8/2011 | Watanabe | |
| 2001/0052930 A1 | 12/2001 | Adair et al. | |
| 2002/0003928 A1 | 1/2002 | Bischel et al. | |
| 2002/0087149 A1 | 7/2002 | McCary | |
| 2002/0137984 A1 | 9/2002 | Chhibber et al. | |
| 2003/0112421 A1 | 6/2003 | Smith | |
| 2003/0132701 A1 | 7/2003 | Sato et al. | |
| 2003/0147254 A1 | 8/2003 | Yoneda et al. | |
| 2003/0169603 A1 | 9/2003 | Luloh et al. | |
| 2003/0223248 A1 | 12/2003 | Cronin et al. | |
| 2003/0223249 A1 | 12/2003 | Lee et al. | |
| 2004/0004846 A1 | 1/2004 | Steen et al. | |
| 2004/0090796 A1 | 5/2004 | Steen et al. | |
| 2004/0124429 A1 | 7/2004 | Stokes et al. | |
| 2004/0233655 A1 | 11/2004 | Zimmerman et al. | |
| 2005/0018309 A1 | 1/2005 | McGuire, Jr. et al. | |
| 2005/0024587 A1 | 2/2005 | Somani | |
| 2005/0047172 A1 | 3/2005 | Sander | |
| 2005/0063171 A1 | 3/2005 | Leitel et al. | |
| 2005/0099824 A1 | 5/2005 | Dowling et al. | |
| 2005/0110808 A1 | 5/2005 | Goldschmidt et al. | |
| 2005/0140270 A1 | 6/2005 | Henson et al. | |
| 2005/0190562 A1 | 9/2005 | Keuper et al. | |
| 2005/0243539 A1 | 11/2005 | Evans et al. | |
| 2005/0270775 A1 | 12/2005 | Harbers et al. | |
| 2006/0203468 A1 | 9/2006 | Beeson et al. | |
| 2006/0262272 A1 | 11/2006 | Anderson et al. | |
| 2007/0102033 A1 | 5/2007 | Petrocy | |
| 2007/0133211 A1 | 6/2007 | Yoneda et al. | |
| 2007/0213618 A1 | 9/2007 | Li et al. | |
| 2007/0219417 A1 | 9/2007 | Roberts et al. | |
| 2007/0273290 A1 | 11/2007 | Ashdown et al. | |
| 2007/0284597 A1 | 12/2007 | Nawashiro et al. | |
| 2007/0291491 A1 | 12/2007 | Li et al. | |
| 2008/0030984 A1 | 2/2008 | Harbers et al. | |
| 2008/0073616 A1 | 3/2008 | Dong et al. | |
| 2008/0112153 A1 | 5/2008 | Iwasaki et al. | |
| 2008/0144169 A1 | 6/2008 | Zahniser et al. | |
| 2008/0175002 A1 | 7/2008 | Papac et al. | |
| 2008/0208006 A1 | 8/2008 | Farr | |
| 2008/0246919 A1 | 10/2008 | Smith | |
| 2008/0246920 A1 | 10/2008 | Buczek et al. | |
| 2008/0262316 A1 | 10/2008 | Ajima et al. | |
| 2008/0291682 A1 | 11/2008 | Falicoff et al. | |
| 2009/0036955 A1 | 2/2009 | Han | |
| 2009/0054957 A1 | 2/2009 | Shanbaky | |
| 2009/0092750 A1 | 4/2009 | Yang et al. | |
| 2009/0095960 A1 | 4/2009 | Murayama | |
| 2009/0105698 A1 | 4/2009 | Hodel et al. | |
| 2009/0154137 A1 | 6/2009 | Bierhuizen et al. | |
| 2009/0154192 A1 | 6/2009 | Krattiger | |
| 2009/0161358 A1 * | 6/2009 | Tsutsui et al. | 362/234 |
| 2009/0168395 A1 | 7/2009 | Mrakovich et al. | |
| 2009/0182313 A1 | 7/2009 | Auld | |
| 2009/0190371 A1 | 7/2009 | Root | |
| 2009/0203966 A1 | 8/2009 | Mizuyoshi | |
| 2009/0219586 A1 | 9/2009 | Fujimoto et al. | |
| 2009/0227847 A1 | 9/2009 | Tepper et al. | |
| 2009/0267088 A1 | 10/2009 | Peng et al. | |
| 2010/0100006 A1 | 4/2010 | Xu et al. | |
| 2010/0127299 A1 | 5/2010 | Smith et al. | |
| 2010/0182569 A1 | 7/2010 | Artsyukhovich et al. | |
| 2010/0228089 A1 | 9/2010 | Hoffman et al. | |
| 2010/0317923 A1 | 12/2010 | Endo et al. | |
| 2011/0009752 A1 | 1/2011 | Chen et al. | |
| 2011/0037948 A1 | 2/2011 | Horvath et al. | |
| 2011/0037949 A1 | 2/2011 | Papac et al. | |
| 2011/0038174 A1 | 2/2011 | Papac et al. | |
| 2011/0122366 A1 | 5/2011 | Smith | |
| 2011/0149246 A1 | 6/2011 | Artsyukhovich | |
| 2011/0149591 A1 | 6/2011 | Smith | |

OTHER PUBLICATIONS

PCT/US2012/052200 International Search Report dated Oct. 26, 2012.

Liu, C.K., et al.; "High Efficiency Silicon-Based High Power LED Package Integrated with Micro-Thermoelectric Device"; Microsystems Packaging, Assembly and Circuits Technology; IMPACT 2007. Abstract only—worldwide web: www.ieee.org. DOI 10.1109/IMPACT2007.4433562.

* cited by examiner

LED ILLUMINATOR

RELATED APPLICATION INFORMATION

This application is a continuation-in-part of U.S. application Ser. No. 13/208,974 filed on Aug. 12, 2011 now abandoned which claims priority to U.S. Provisional Application Ser. No. 61/378,206 filed Aug. 30, 2010, each of which are hereby fully incorporated herein by reference.

BACKGROUND

Anatomically, an eye may be divided into two distinct parts—an anterior segment and a posterior segment. The anterior segment includes a lens and extends from an outermost layer of the cornea (the corneal endothelium) to a posterior of a lens capsule. The posterior segment includes a portion of the eye behind the lens capsule. The posterior segment extends from an anterior hyaloid face (part of a vitreous body) to a retina, with which a posterior hyaloid face is in direct contact. The posterior segment is much larger than the anterior segment.

The posterior segment includes the vitreous body—a clear, colorless, gel-like substance. It makes up approximately two-thirds of the eye's volume, giving it form and shape before birth. The vitreous body is composed of 1% collagen and sodium hyaluronate and 99% water. The anterior boundary of the vitreous body is the anterior hyaloid face, which touches the posterior capsule of the lens, while the posterior hyaloid face forms its posterior boundary, and is in contact with the retina. The vitreous body is not free flowing like the aqueous humor and has normal anatomic attachment sites. One of these sites is the vitreous base, which is an approximately 3-4 mm wide band that overlies the ora serrata. The optic nerve head, macula lutea, and vascular arcade are also sites of attachment. The vitreous body's major functions are to hold the retina in place, maintain the integrity and shape of the globe, absorb shock due to movement, and to give support for the lens posteriorly. In contrast to the aqueous humor, the vitreous body is not continuously replaced. The vitreous body becomes more fluid with age in a process known as syneresis. Syneresis results in shrinkage of the vitreous body, which can exert pressure or traction on its normal attachment sites. If enough traction is applied, the vitreous body may pull itself from its retinal attachment and create a retinal tear or hole.

Various surgical procedures, called vitreo-retinal procedures, are commonly performed in the posterior segment of the eye. Vitreo-retinal procedures are appropriate to treat many serious conditions of the posterior segment. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

A surgeon performs vitreo-retinal procedures with a microscope and special lenses designed to provide a clear image of the posterior segment. Several tiny incisions just a millimeter or so in length are made on the sclera at the pars plana. The surgeon inserts microsurgical instruments through the incisions, such as a fiber optic light source, to illuminate inside the eye; an infusion line to maintain the eye's shape during surgery; and instruments to cut and remove the vitreous body.

During such surgical procedures, proper illumination of the inside of the eye is important. Typically, a thin optical fiber is inserted into the eye to provide the illumination. A light source, such as a halogen tungsten lamp or high pressure arc lamp (metal-halides, Xe), may be used to produce the light carried by the optical fiber into the eye. The light passes through several optical elements (typically lenses, mirrors, and attenuators) and is transmitted to the optical fiber that carries the light into the eye. The advantage of arc lamps is a small emitting area (<1 mm), a color temperature close to daylight, and typically a longer life than halogen lamps (i.e., 400 hours vs. 50 hours). The disadvantage of arc lamps is high cost, decline in power, complexity of the systems and the need to exchange lamps several times over the life of the system.

In an effort to overcome some of the limitations of halogen tungsten lamps and high pressure arc lamps, other light sources, such as light emitting diodes (LEDs), may be used to produce the light transmitted through the optical fiber into the eye. LED based illuminators may be provided at considerably lower cost and complexity, and may exhibit characteristic life times of 50,000 to 100,000 hours, which may enable operating an ophthalmic fiber illuminator for the entire life of the instrument with very little drop in output and without the need to replace LEDs. LED light sources, however, generally exhibit lower luminous efficiency and decreased luminous flux than comparable halogen tungsten lamps and high pressure arc lamps.

DETAILED DESCRIPTION

Figure 1:
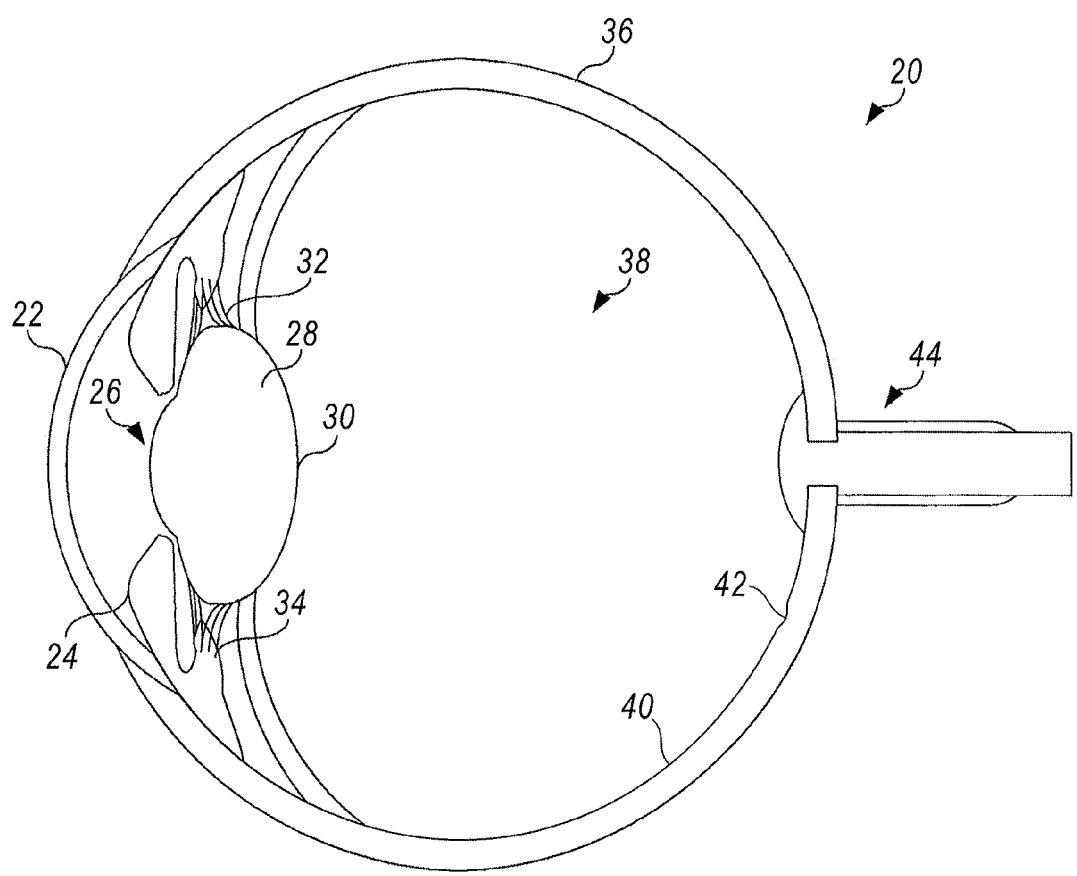
FIG. 1 is a cross-sectional view of an eye illustrating its internal anatomy.

Referring now to the discussion that follows, and also to the drawings, illustrative approaches to the disclosed systems and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive, otherwise limit, or restrict the claims to the precise forms and configurations shown in the drawings and disclosed in the following detailed description.

FIG. 1 illustrates an anatomy of an eye 20, which includes a cornea 22, an iris 24, a pupil 26, a lens 28, a lens capsule 30, zonules 32, ciliary body 34, sclera 36, vitreous region 38, retina 40, macula 42, and optic nerve 44. Cornea 22 is a clear, dome shaped structure on the surface of eye 20 that acts as a window, letting light into the eye. Iris 24, which corresponds to the colored part of the eye, is a muscle surrounding pupil 26 that relaxes and contracts to control the amount of light entering eye 20. Pupil 26 is a round, central opening in iris 24. Lens 28 is a structure inside eye 20 that helps focus light on retina 40. Lens capsule 30 is an elastic bag that encapsulates lens 30, helping to control the shape of lens 28 as the eye focuses on objects at different distances. Zonules 32 are slender ligaments that attach lens capsule 30 to the inside of eye 20, holding lens 28 in place. Ciliary body 34 is a muscular area attached to lens 28 that contracts and relaxes to control the size of the lens for focusing. Sclera 36 is a tough, outermost layer of eye 20 that maintains the shape of the eye. Vitreous region 38 is a large, gel-filled section located towards a back of eye 20 that helps maintain the curvature of the eye. Retina 40 is a light-sensitive nerve layer at the back of eye 20 that receives light and converts it into signals to send to the brain. Macula 42 is an area in the back of eye 20 that includes receptors for detecting fine detail in a viewed image. Optic nerve 44 transmits signals from eye 20 to the brain.

Figure 2:
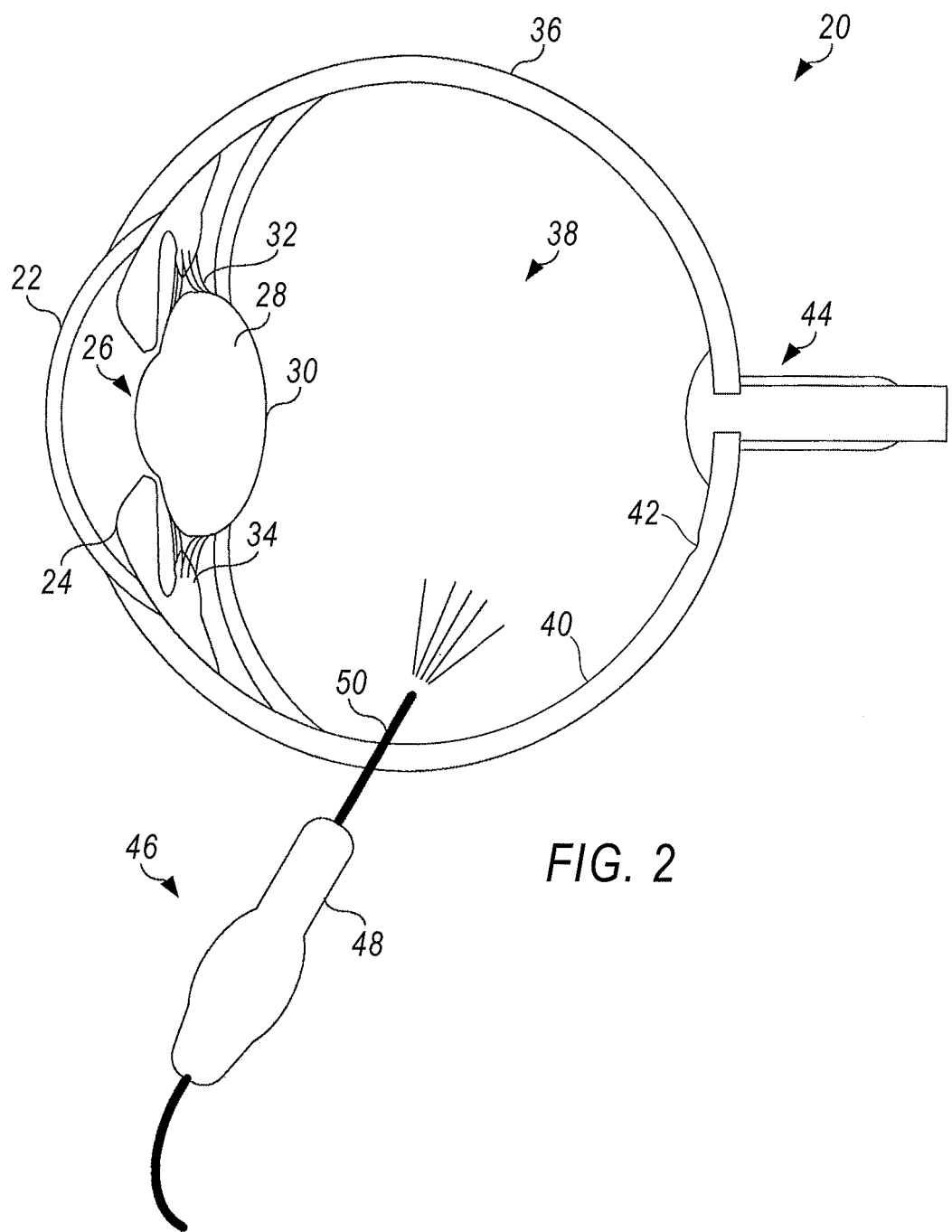
FIG. 2 is a schematic illustration of an exemplary illumination probe that may be employed with an endoilluminator, shown illuminating an interior region of the eye of FIG. 1.

With reference to FIG. 2, an ophthalmic endoilluminator 46 for illuminating an interior of eye 20 is shown inserted through sclera 36 into vitreous region 38. Endoilluminator 46 may include a handpiece 48 and a probe 50. Probe 50 may include a fiber optic cable 52 for transferring light from an illuminator to illuminate the inside of vitreous region 38 of eye 20 during various intra-optical procedures, such as vitreoretinal surgery.

Endoilluminator 46 may employ various light sources, for example, halogen tungsten lamps and high-pressure arc lamp (metal-halides and Xe). Light emitting diodes (LEDs) may also be employed as a light source for endoilluminator 46. LEDs may provide considerably lower cost and complexity than comparable halogen tungsten lamps and high-pressure arc lamps. LEDs may have characteristic life times of 50,000-100,000 hours, which would enable operating ophthalmic endoilluminator 46 for the life of the instrument with minimal drop in output and without a need for replacing LEDs.

Figure 3:
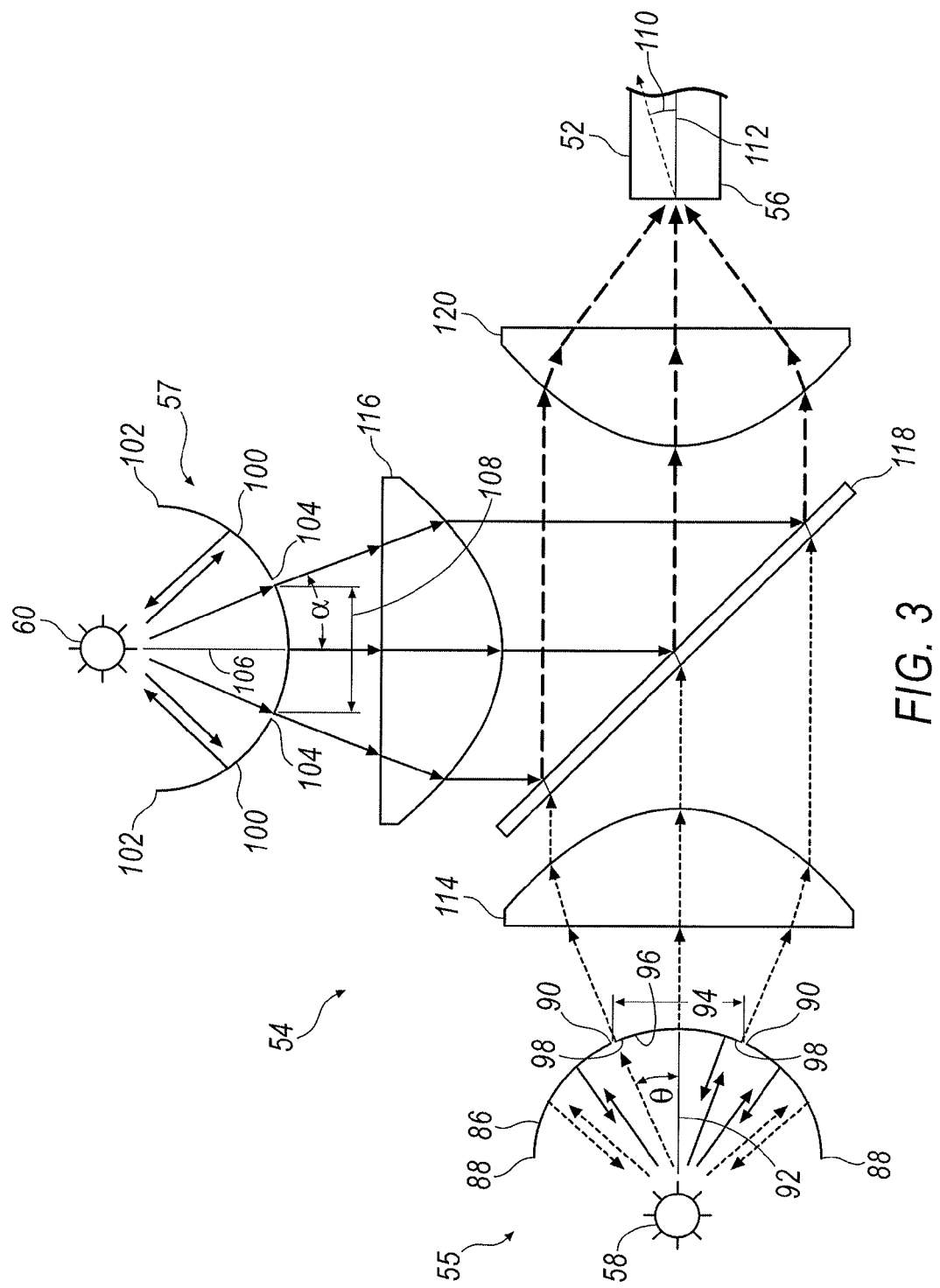
FIG. 3 is a schematic partial cross-sectional view of an exemplary illuminator that may be employed with an endoilluminator for supplying light to the illumination probe of FIG. 2.

Referring to FIG. 3, endoilluminator 46 may employ an illuminator 54 for producing light at a particular luminous flux and chromaticity. Light generated by illuminator 54 may be transmitted to probe 50 through fiber optic cable 52, which may have an end 56 optically connected to illuminator 54. The exemplary configuration shown in FIG. 3 employs a first light channel 55 and a second light channel 57. First light channel 55 includes a first light source 58, and second light channel 57 includes a second light source 60. Additional light sources may also be employed depending on the design requirements of a particular application. Light sources 58 and 60 may be similarly configured or have different configurations.

Figure 4:
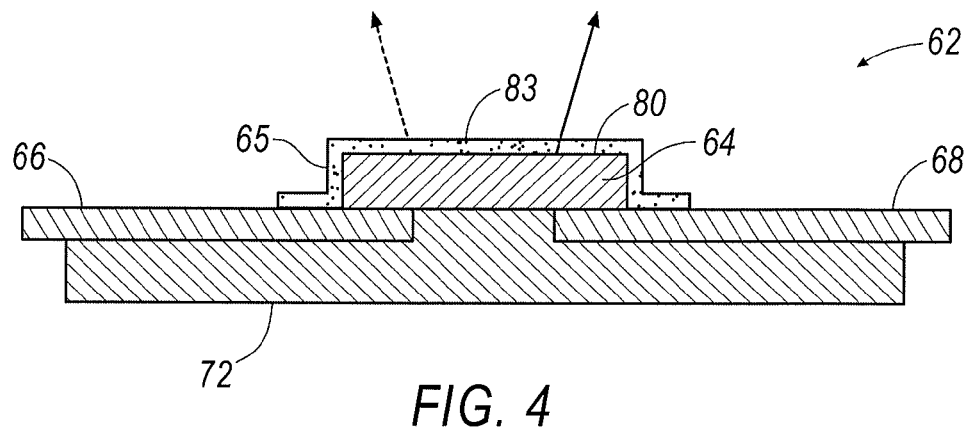
FIG. 4 is a schematic illustration of an exemplary undomed light emitting diode (LED) that may be employed with the illuminator of FIG. 3.

Light source 58 may include one or more LEDs configured to emit a generally broad-spectrum white light. The LEDs may be manufactured in a variety of configurations. An exemplarily configured LED 62 is illustrated in FIG. 4. LED 62 may be produced by coating a generally monochromatic LED die 64, with a wavelength converting material 65 capable of converting electromagnetic radiation, in a particular range of the electromagnetic spectrum, to another range within the electromagnetic spectrum, including but not limited to, the conversion of high-energy particle rays, x-rays and UV to lower energy photons. Any suitable type of wavelength converting material or substance may be employed. The luminescence process utilized for conversion may be based on either slow emission (Phosphorescence) or fast emission (fluorescence), depending on the type of wavelength converting materials employed.

LED die 64 generally emits light within a relatively narrow range of wavelengths, such as ultraviolet (UV), violet, or blue light, depending on the semiconductor diode material employed. For example, Indium Gallium Nitride (InGaN) generally produces a blue light having a wavelength ($\lambda$) of approximately 450 nm<$\lambda$<500 nm. The relatively narrow light band is generally not suitable for illumination. The emitted spectrum may be tailored by employing, for example, phosphor of different colors as wavelength converting material 65 to produce light across a desired spectrum. The number and type of phosphor coatings employed may be varied to produce light within a desired wavelength range. A phosphor material that may be employed with a blue semiconductor diode material to produce a generally broad-spectrum white light is cerium doped yttrium aluminum garnet ($Ce^{3+}$:YAG). The phosphor coating causes a portion of the blue light emitted from LED die 64 to undergo a Stokes shift. The Stokes-shifted light emits at a higher wavelength range tending toward the yellow spectrum than the blue light emitted directly from the InGaN semiconductor. Not all of the blue light emitted from the semiconductor undergoes a Stokes-shift. Unconverted blue light and the Stokes-shifted light combine to produce light that appears generally as broadband white light. The phosphor coating for converting a portion of the blue light emitted from LED die 64 to a higher wavelength light may be deposited on a surface 80 of the LED die. This is merely one example of various semiconductor/phosphor combinations that may be employed to produce a broadband white light.

With continued reference to FIG. 4, LED die 64 may be electrically connected to a cathode 66 and an anode 68. LED die 64, cathode 66 and anode 68 may be supported on a substrate 72. Applying an electrical current to cathode 66 and anode 68 causes LED die 64 to emit light within a wavelength range corresponding to the semiconductor diode material employed.

Figure 5:
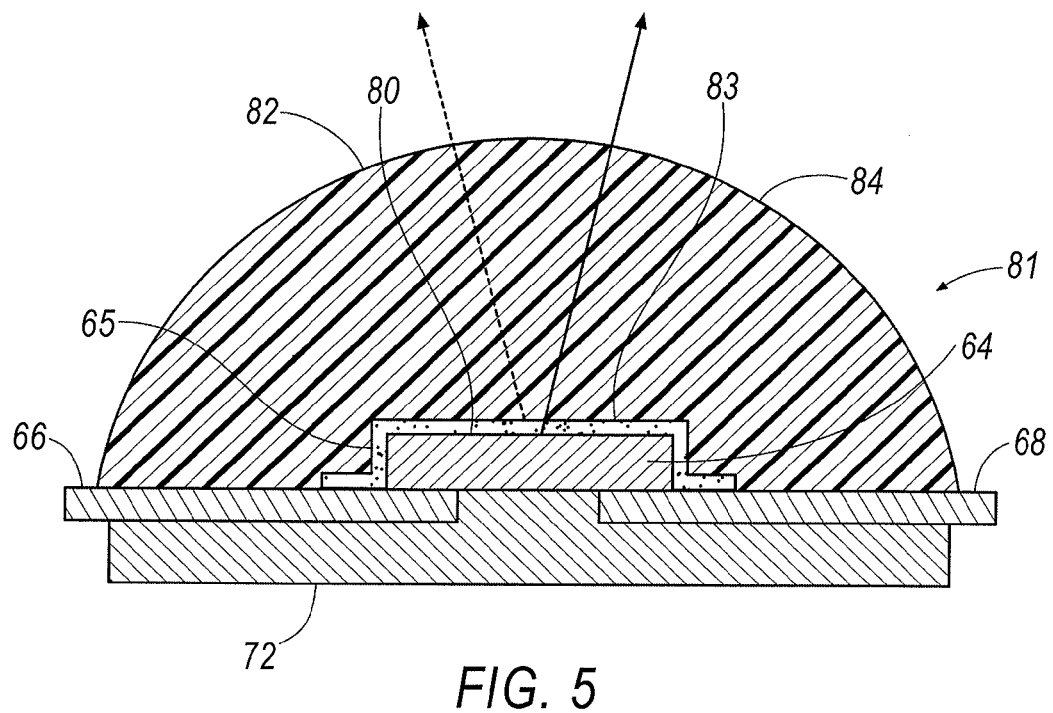
FIG. 5 is a schematic illustration of an exemplary domed light emitting diode (LED) that may be employed with the illuminator of FIG. 3.

LEDs employed with light source 58 may also be configured to include a lens for further controlling the light emitted from the light source. LEDs employing a lens may be referred to as "domed" LEDs. An example of a domed LED 81 is illustrated in FIG. 5. Domed LED 81 may have as similar configuration as undomed LED 62 shown in FIG. 4, but with the addition of a lens 82 attached to LED die 64. Materials used to make wavelength converting material 65 typically have high refractive indices, which may result in a portion of the light directly emitted from LED die 64 being reflected back onto the LED (i.e., recycled) at the wavelength converting material/air surface interface (i.e., surface 83 of wavelength converting material 65). Recycling light produced by LED die 64 may cause a shift in the chromaticity of the light emitted from the LED towards the yellow spectrum (for example, when employing $Ce^{3+}$:YAG as the phosphor) due to a portion of the recycled light undergoing a Stokes shift. Light recycling may be reduced by attaching lens 82 to undomed LED 62 to produce domed LED 81. Lens 82 includes a convex outer surface 84 that tends to reduce light recycling within domed LED 81.

For convenience, light having a wavelength range produced by LED die 64 shall hereinafter be referred to as "unconverted light", whereas light having a wavelength within the range of the Stokes-shifted light emitted from the phosphor coating (i.e., wavelength converting material 65)

shall herein after be referred to as "converted light". Furthermore, light having a wavelength within the range produced by LED die 64 (i.e., unconverted light) is represented throughout the figures by a solid line, and light having a wavelength within the range of the Stokes-shifted light (i.e., converted light) is represented throughout the figures by a small dashed line.

Continuing to refer to FIG. 3, light channel 55 may include various features for enhancing the light flux emitted from the light channel, and for controlling the size and direction of a corresponding light beam. For example, light channel 55 may include one or more reflective optical elements 86 arranged adjacent to light source 58. Reflective optical element 86 may be configured as a broadband reflector to reflect both converted and unconverted light back toward light source 58. Reflective optical element 86 is generally spaced apart from light source 58, and may have a generally concave shape relative to light source 58. Reflective optical element 86 includes a first circumferential edge defining a proximal end 88, and second circumferential edge defining an opposite distal end 90. Proximal end 88 may be arranged axially along an optical axis 92 in a general vicinity of light source 58. Distal end 90 may be arranged along optical axis 92 at a an axial distance from light source 58 that is greater than an axial distance between proximal end 88 and light source 58. Due to the curvature of reflective optical element 86, a radial distance between proximal end 88 and optical axis 92 is greater than a radial distance between distal end 90 and optical axis 92.

Continuing to refer to FIG. 3, arranged within an opening 94 of reflective optical element 86 is a dichroic mirror 96. Dichroic mirror 96 may be configured to allow converted light to pass through dichroic mirror 96, and to reflect unconverted light back toward light source 58. Reflective optical element 86 and dichroic mirror 96 together operate to enhance the light flux emitted from light channel 55, which may improve the operating efficiency of illuminator 54. Dichroic mirror 96 and reflective optical element 86 also operate together to direct converted light out through opening 94 in reflective optical element 86.

Dichroic mirror 96 may have a generally concave shape relative to light source 58. For example, dichroic mirror 96 may be configured as a substantially spherical reflector having a center of curvature arranged along outer surface 83 of wavelength converting material 65 and generally centered relative to LED die 64. Dichroic mirror 96 is generally displaced away from light source 58. In the exemplary configuration illustrated in FIG. 3, substantially the entire dichroic mirror 96 is positioned at a distance further from light source 58 than distal end 90 of reflective optical element 86. Dichroic mirror 96 may also be positioned at other locations along optical axis 92 relative to distal end 90 of reflective optical element 86, which may include positions that are closer or further away from light source 58. For example, all or a portion of dichroic mirror 96 may be positioned along optical axis 92 between light source 58 and distal end 90 of reflective optical element 86. Dichroic mirror 96 may be sized so as not to overlap reflective optical element 86, as shown in FIG. 3, or may be sized to overlap reflective optical element 86, in which case an edge 98 of dichroic mirror 96 would be at a further distance from optical axis 92 than distal end 90 of reflective optical element 86. First reflective optical element 86 and dichroic mirror 94 may also be integrally formed, for example, by applying optical coatings associated with the individual optical elements to a continuous uninterrupted substrate material.

Employing undomed LED 62 (FIG. 4) as light source 58 with reflective optical element 86 may enhance the luminous flux emitted from light channel 55, but may also cause a shift in the chromaticity of light emitted from light channel 55 toward the yellow wavelength ranges, as opposed to a similar configuration, for example, employing domed LED 81 without reflective optical element 86. As discussed previously, operating an LED without a lens may cause a shift in the wavelength of the emitted light toward the yellow wavelength ranges due to recycling of a portion of the light emitted from LED die 64. Employing reflective optical element 86 with either undomed LED 62 (FIG. 4) or domed LED 81 (FIG. 5) also tends to cause a shift in the chromaticity of light emitted from light channel 55 toward the yellow wavelength ranges.

Figure 6:
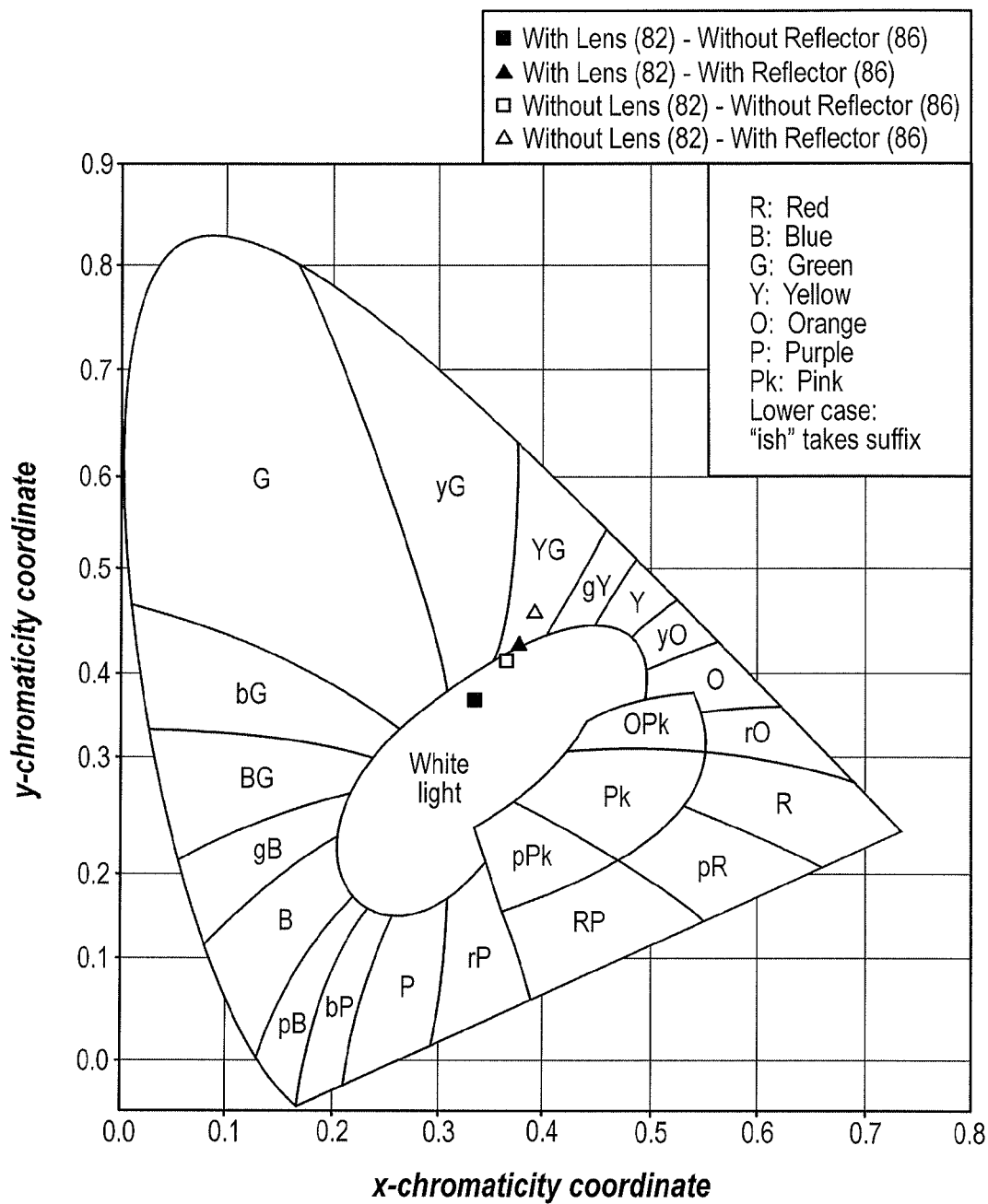
FIG. 6 is a chromaticity diagram graphically depicting an exemplary relative effect that certain individual features of the illuminator of FIG. 3 may have on chromaticity.
Figure 7:
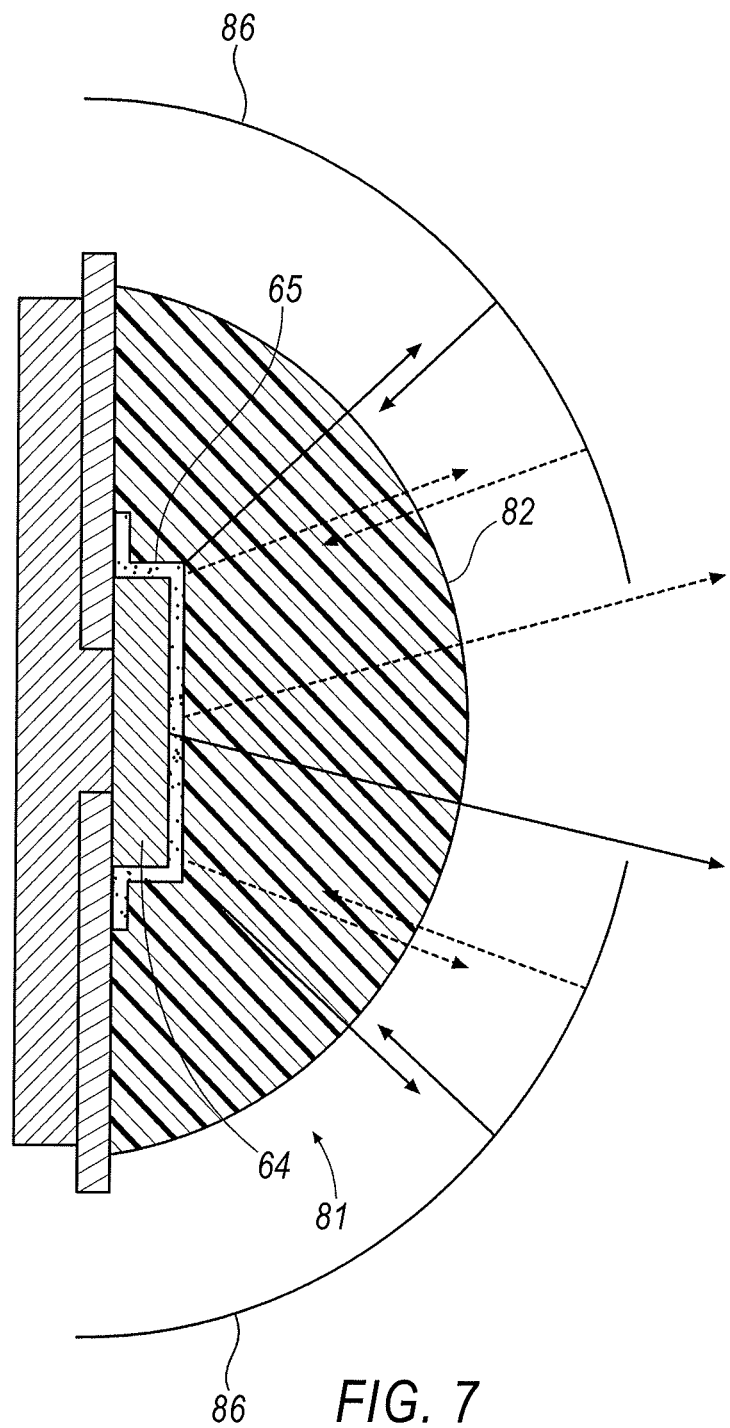
FIG. 7 is a schematic partial cross-sectional view of the exemplary domed LED of FIG. 5 employed with a reflective optical element.
Figure 8:
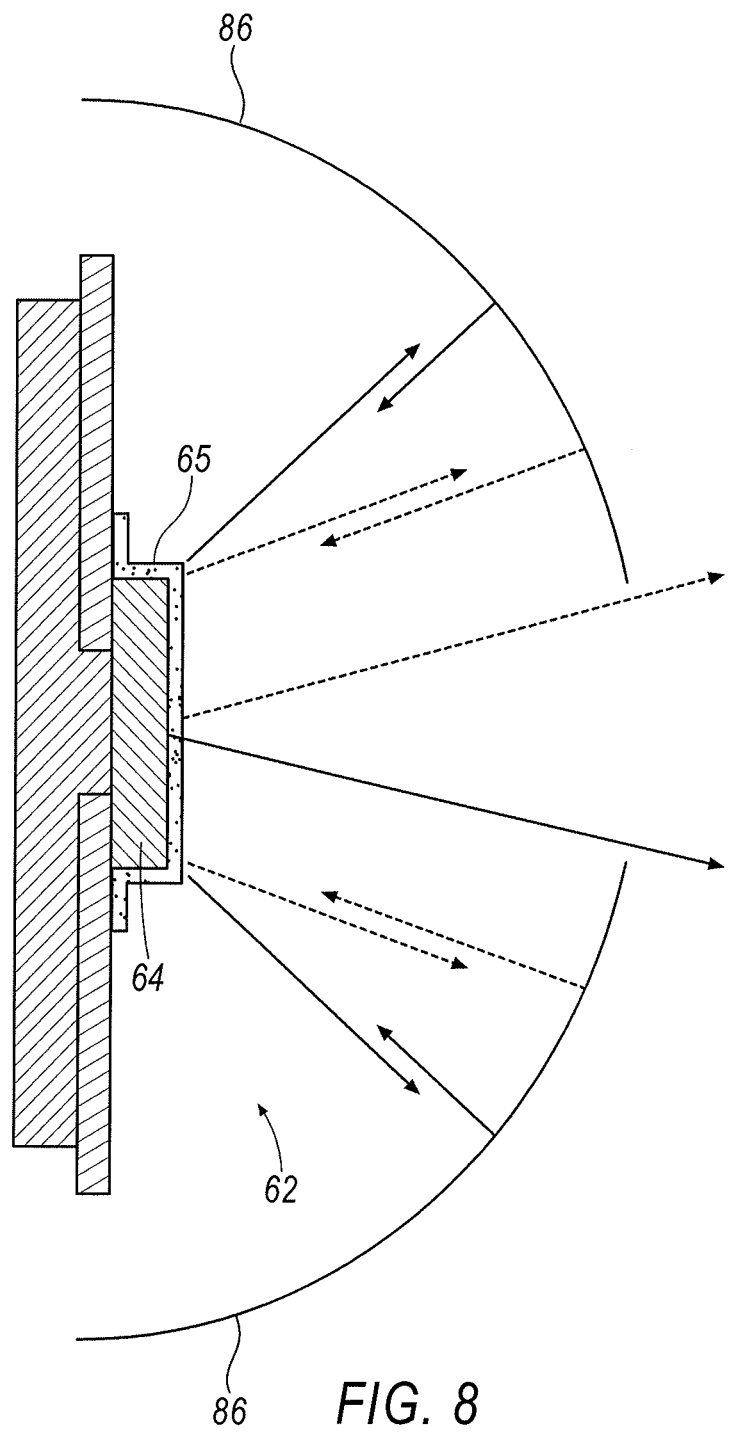
FIG. 8 is a schematic partial cross-sectional view of the exemplary undomed LED of FIG. 4 employed with a reflective optical element.

A representative shift in chromaticity that may occur when employing reflective optical element 86 with either undomed LED 62 or domed LED 81 is reflected on a chromaticity diagram show in FIG. 6. Included in the chromaticity diagram is a CIE 1931 color space identifying the range of colors typically visible to a human eye. An exemplary chromaticity of light emitted from domed LED 81 (FIG. 5) is indicated on the chromaticity chart as a solid black square. An exemplary chromaticity of light emitted from undomed LED 62 (FIG. 4) is indicated on the chromaticity chart as an unfilled square. Employing reflective optical element 86 (FIG. 3) with domed LED 81, for example, as shown in FIG. 7, or undomed LED 62, for example, as shown in FIG. 8, may increase recycling of light emitted from the corresponding LED, resulting in a shift in chromaticity of the emitted light toward the yellow frequency range. An exemplary chromaticity of light emitted from domed LED 81 when used in connection with reflective optical element 86 (FIG. 7) is indicated on the chromaticity chart as a solid black triangle. An exemplary chromaticity of light emitted from undomed LED 62 when used in connection with reflective optical element 86 (FIG. 8) is indicated on the chromaticity chart as an unfilled triangle. Employing reflective optical element 86 with domed LED 81 and undomed LED 62 in both instances will generally produce a measurable shift in chromaticity of light emitted from light channel 55 toward the yellow wavelength ranges.

Continuing to refer to FIG. 3, the chromaticity shifting of light emitted from light channel 55 toward yellow wavelength ranges when employing undomed LED 62 and/or reflective optical element 86 may be at least partially attenuated by employing second light channel 57, which includes second light source 60. To shift the blue wavelength deficient light emitted from light channel 55 back toward more white wavelength ranges, light source 60 may include one or more LEDs configured to emit a narrow band blue light. The light emitted from second light source 60 will generally be at a similar wavelength range as the light blocked by dichroic mirror 96. The LED employed with light source 60 may be manufactured in a variety of configurations, examples of which are shown in FIGS. 4 and 5. LED die 64 may be selected to generally emit light within a similar wavelength range as the semiconductor diode material employed with light source 58. This may be accomplished by employing the same semiconductor diode material for both light sources 58 and 60, or alternatively, by employing different semiconductor materials that emit light within similar wavelength ranges. Unlike the LED employed with light source 58, the LED employed with light source 60 generally does not employ a wavelength converting material or substance for converting the light emitted from the semiconductor diode material to another wavelength range, since the light emitted from light channel 57 will generally have the same wavelength range as the light emitted from the semiconductor diode material employed with light source 58.

Continuing to refer to FIG. 3, light channel 57 may include various features for enhancing the luminous flux emitted from light channel 57, and for controlling the size and direction of a corresponding light beam. For example, light channel 57 may include one or more second reflective optical elements 100 arranged adjacent to light source 60. Reflective optical element 100 may be configured as a broadband or narrow band reflector with sufficient bandwidth to reflect substantially all of the light arriving at the reflector back toward light source 60. Reflective optical element 100 is generally spaced apart from light source 60, and may have a generally concave shape relative to light source 60. Reflective optical element 100 may include a first circumferential edge defining a proximal end 102 and a second circumferential edge defining an opposite distal end 104. Proximal end 102 may be arranged axially along an optical axis 106 in a general vicinity of light source 60. Distal end 104 may be arranged along optical axis 106 at an axial distance from light source 60 that is greater than an axial distance between proximal end 102 and light source 60. Due to the curvature of reflective optical element 100, a radial distance between proximal end 102 and optical axis 106 is greater than a radial distance between distal end 104 and optical axis 106.

Continuing to refer to FIG. 3, reflective optical element 100 may include an optically transparent opening 108 though which light produced by light source 60 may be emitted from light channel 57. Opening 108 may be configured as an aperture extending completely through reflective optical element 100, as shown in FIG. 3. Alternatively, opening 108 may be formed by providing a region corresponding to opening 108 over which no reflective coating is applied to a substantially optically clear substrate of reflective optical element 100. In the latter configuration, the optically clear substrate of reflective optical element 100 will cover opening 108, but since the region corresponding to opening 108 is devoid of a reflective coating, light emitted from light source 60 would be able to pass through the uncoated substrate material.

Light source 60 may emit light over a wide angle. To help maximize the light flux from light channel 57 passing through opening 108, reflective optical element 100 may operate to redirect at least a portion of the light emitted from light source 60 that exceeds a selected emission angle $\alpha$ back towards light source 60. This enables the portion of light emitted form light source 60 at an emission angle greater than a selected maximum to be recycled within light channel 57 and redirected through opening 108 in reflective optical element 100. Recycling at least a portion of the light emitted from light source 60 may increase the light flux emitted from light channel 57.

Illuminator 54 may include one or more optical elements for combining the yellow shifted broad-spectrum light beam emitted from light channel 55 with the narrow blue spectrum light beam emitted from light channel 57 into a single broad-spectrum white light beam suitable for delivery to fiber optic cable 52. Fiber optic cable 52 generally includes a single optical fiber, although multiple optical fibers may also be employed. Fiber optic cable 52 typically includes a maximum emission angle 110, which is an angle relative to a fiber axis 112 at which light may enter the fiber optic wire and travel along its length. A numerical aperture (NA) may be determined for fiber optic cable 52 based on the fiber's maximum emission angle. The NA corresponds to the sine of the fiber optic cable's maximum emission angle. The optical elements for optically connecting light channels 55 and 57 to fiber optic cable 52 may be configure to achieve a numerical aperture compatible with the numerical aperture of fiber optic cable 52. This helps ensure that light delivered to fiber optic cable 52 will be able to enter and travel along fiber optic cable 52.

In the exemplary configuration of illuminator 54 illustrated in FIG. 3, a first collimating lens 114 receives a diverging light beam emitted from light channel 55. Light passing through collimating lens 114 is refracted to form a generally collimated light beam. The maximum incidence angle $\theta$ of the light beam arriving at collimating lens 114 from light channel 55 may be at least partially controlled by varying the size of opening 94 in reflective optical element 86. The maximum incidence angle generally increases with increasing size of opening 94.

A second collimating lens 116 receives a diverging light beam emitted from light channel 57. Light passing through second collimating lens 116 is refracted to form a generally collimated light beam. The maximum incidence angle $\alpha$ of the light beam arriving at collimating lens 116 from light channel 57 may be at least partially controlled by varying the size of opening 108 in reflective optical element 100. The maximum incidence angle generally increases with increasing size of opening 108.

Illuminator 54 may include a dichroic filter 118 for combining the broad-spectrum yellow shifted light beam emitted from light channel 55 with the narrow blue spectrum light beam emitted from light channel 57 to form a single collimated broad-spectrum white light beam. Dichroic filter 118 may be arranged downstream of first collimating lens 114 and second collimating lens 116. Dichroic filter 118 may be configured to selectively pass light falling within the wavelength range of light emitted from light channel 55, while reflecting light falling within the wavelength range of light emitted from light channel 57. The collimated light beam from first collimating lens 114 passes through dichroic filter 118, whereas the collimated light beam from second collimating lens 116 is reflected from dichroic filter 118, thereby enabling the two separate light beams to combine and form a single collimated light beam that generally appears as a broad-spectrum white light. The resulting broad-spectrum white light beam is represented in FIG. 3 by long dashed lines. The collimated broad-spectrum white light beam from dichroic filter 118 passes through a condensing lens 120, which operates to focus the collimated light beam for delivery to fiber optic cable 52.

FIG. 3 illustrates merely one example of an optical arrangement for combining the light emitted from light channel 55 with the light emitted from light channel 57, and focusing the resulting light beam for transmission to fiber optic cable 52. Other arrangements may also be employed.

Figure 9:
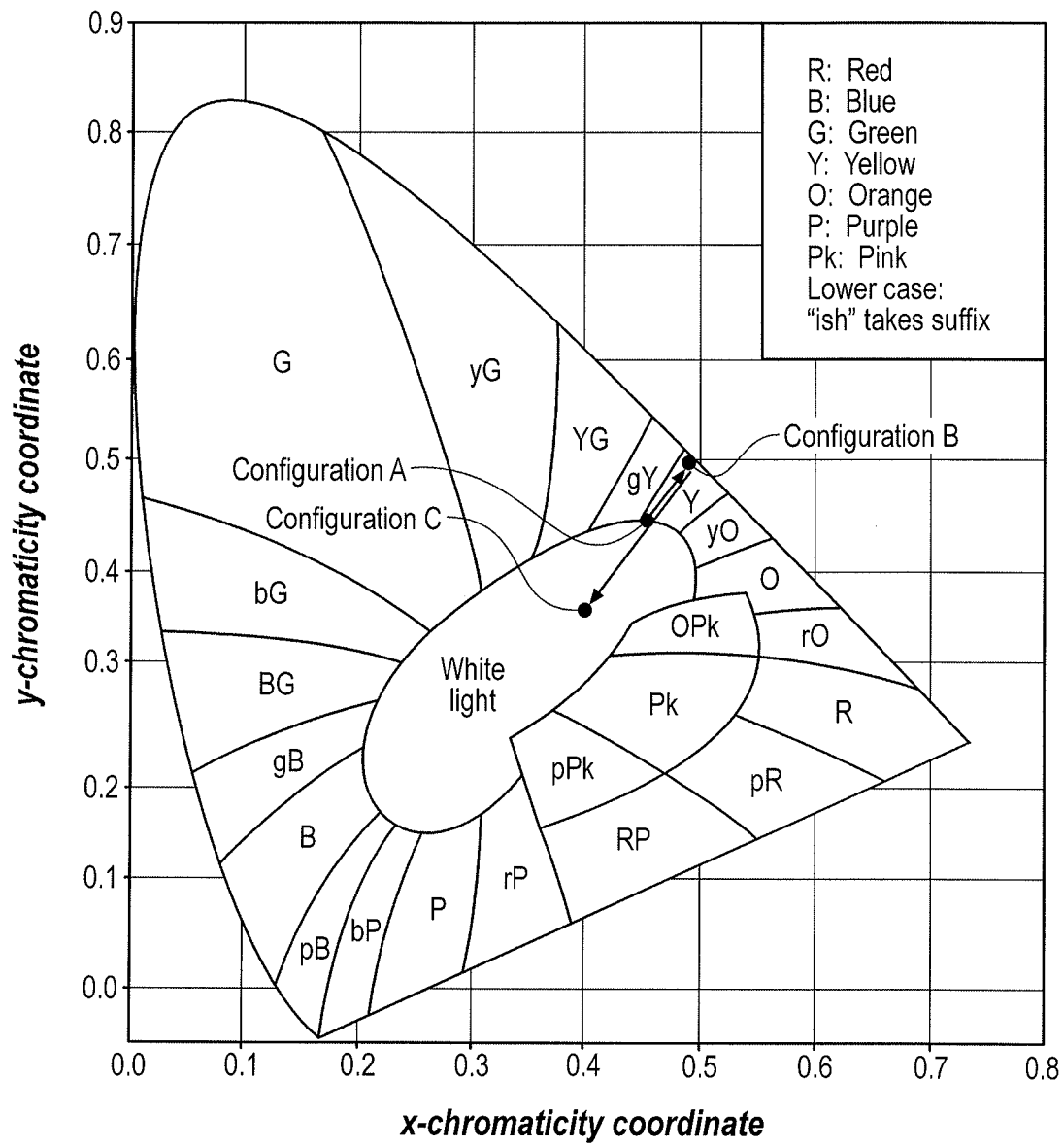
FIG. 9 is a chromaticity diagram graphically depicting relative changes in chromaticity that may be achieved when employing the exemplary illuminator of FIG. 3.

Representative examples of the relative improvement in chromaticity and luminous flux that may occur when employing illuminator 54 are reflected in the chromaticity diagram shown in FIG. 9. Included in the chromaticity diagram is the CIE 1931 color space identifying the range of colors typically visible to a human eye. Exemplary chromaticity levels for three different illuminator configurations are plotted on the chromaticity diagram. The three illuminator configurations are identified as configurations A, B and C. With reference to FIG. 3, "Configuration A" generally consists of LED light source 58 configured as undomed LED 62 (FIG. 4), reflective optical element 86, first collimating lens 114 and condensing lens 120, without dichroic mirror 96, dichroic filter 118, and second light channel 57. "Configuration B" is similar to "Configuration A", but also includes dichroic mirror 96. "Configuration C" is substantially the configuration illustrated in FIG. 3. Assuming a light flux of 100 percent for "Configuration A", adding dichroic mirror 96 to "Configuration A" to arrive at "Configuration B" may produce an exemplary increase in luminous flux of approximately 1.8 percent, but also produces a corresponding shift in chromaticity towards longer yellow wavelengths. Modifying "Configuration B" to include light channel 57 and dichroic filter 118 may result in a 9.2 percent increase in luminous flux, as compared to "Configuration A", while at same time shifting chromaticity significantly toward the white light wavelengths.

It will be appreciated that the exemplary LED illuminator described herein has broad applications. The foregoing configuration were chosen and described in order to illustrate principles of the methods and apparatuses as well as some practical applications. The preceding description enables others skilled in the art to utilize methods and apparatuses in various configurations and with various modifications as are suited to the particular use contemplated. In accordance with the provisions of the patent statutes, the principles and modes of operation of the disclosed LED illuminator have been explained and illustrated in exemplary configurations.

It is intended that the scope of the present methods and apparatuses be defined by the following claims. However, it must be understood that the disclosed LED illuminator may be practiced otherwise than is specifically explained and illustrated without departing from its spirit or scope. It should be understood by those skilled in the art that various alternatives to the configuration described herein may be employed in practicing the claims without departing from the spirit and scope as defined in the following claims. The scope of the disclosed LED illuminator should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the device and that the method and apparatus within the scope of these claims and their equivalents be covered thereby. In sum, it should be understood that the device is capable of modification and variation and is limited only by the following claims.

What is claimed is:

1. An illumination device comprising:
a first light source configured to emit light at a first wavelength range and a second wavelength range, the first light source comprising:
a light emitting diode configured to emit light at substantially the first wavelength range; and
a wavelength converting material configured to convert the light emitted by the light emitting diode to light at substantially the second wavelength range;
a first dichroic optical element associated with the first light source, the first dichroic optical element configured to pass the light emitted at the second wavelength range and to block the light emitted at the first wavelength range;
a second light source configured to emit light at the first wavelength range; and
a second dichroic optical element disposed in a light path of the first light source and a light path of the second light source, the optical system configured pass light emitted at the second wavelength range and to reflect light emitted at the first wavelength range in order to optically combine light passing through the first dichroic optical element with light emitted from the second light source.

2. The illumination device of claim 1, further comprising:
a first collimating lens disposed in a light path between the first light source and the second dichroic optical element; and
a second collimating lens disposed in a light path between the second light source and the second dichroic optical element.

3. The illumination device of claim 1, further comprising:
a condensing lens for optically connecting the first and second light sources to a fiber optic cable, the condensing lens disposed in a light path between the second dichroic optical element and the fiber optic cable.

4. The illumination device of claim 1, further comprising a first reflective optical element arranged adjacent the first light source, the first reflective optical element configured to reflect light emitted from the first light source over the entire second wavelength range.

5. The illumination device of claim 1, further comprising a second reflective optical element arranged adjacent the second light source, the second reflective optical element configured to reflect light emitted from the second light source over the entire first wavelength range.

6. The illumination device of claim 4, wherein the first reflective optical element includes a first region arranged at a first axial point along an optical axis of the first light source and a second region arranged at a second axial point along the optical axis of the first light source, a distance along the optical axis from the first axial point to the first light source being less than a distance along the optical axis from the second axial point to the first light source, and a distance from the first axial point to the first region of the reflective optical element being greater than a distance from the second axial point to the second region of the reflective optical element.

7. The illumination device of claim 6, wherein the second reflective optical element includes a proximal end and an opposite distal end, a distance along the optical axis from the distal end of the reflective optical element to the first light source being greater than a distance along the optical axis from the proximal end of the reflective optical element to the first light source, wherein at least a portion of the first dichroic optical element is disposed along the optical axis at a distance from the first light source that is greater than the distance along the optical axis from the first light source to the distal end of the reflective optical element.

8. An illumination device comprising:
a first light source configured to emit a first portion of light in a first wavelength range and a second portion of light in a second wavelength range;
a first reflective element optically associated with the first light source, the first reflective element configured to reflect light in the first and second wavelength ranges;
a first dichroic element optically associated with the first light source, the first dichroic element configured to block light in the first wavelength range, and to pass light in the second wavelength range;
a second light source configured to emit light in the first wavelength range;
a second reflective element optically associated with the second light source, the second reflective element configured to reflect light in at least the first wavelength range; and a second dichroic element disposed in a light path of the first light source and a light path of the second light source.

9. The illumination device of claim 8, wherein the second dichroic element is configured to pass light within the second wavelength range, and to reflect light within the first wavelength range, the second dichroic element operating to optically combine light passing through the first dichroic element with light emitted from the second light source.

10. The illumination device of claim 8, further comprising:
   a first collimating lens disposed in a light path between the first light source and the second dichroic element; and
   a second collimating lens disposed in a light path between the second light source and the second dichroic element.

11. The illumination device of claim 10, further comprising a condensing lens for optically connecting the first and second light sources to a fiber optic wire, the condensing lens disposed in a light path between the second dichroic element and the fiber optic wire.

12. The illumination device of claim 8, wherein the second reflective element includes an aperture for enabling light emitted from the second light source to bypass the second reflective element.

13. The illumination device of claim 8, wherein at least one of the first and second light sources includes a light emitting diode.

* * * * *